US00PP30173P2

(12) United States Plant Patent
Kordes

(10) Patent No.: US PP30,173 P2
(45) Date of Patent: Feb. 5, 2019

(54) GRANDIFLORA ROSE PLANT NAMED 'KORMONALI'

(50) Latin Name: *Rosa hybrida*
Varietal Denomination: KORmonali

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/731,760

(22) Filed: Jul. 31, 2017

(51) Int. Cl.
*A01H 5/02* (2018.01)

(52) U.S. Cl.
USPC ..... Plt./134
CPC ..... *A01H 5/02* (2013.01)

(58) Field of Classification Search
USPC ..... Plt./134
CPC ..... A01H 5/0222
See application file for complete search history.

*Primary Examiner* — Kent L Bell
(74) *Attorney, Agent, or Firm* — Buchanan Ingersoll & Rooney PC

(57) ABSTRACT

A new and distinct variety of Grandiflora Rose Plant, herein referred to by its cultivar name, 'KORmonali', is provided which forms in abundance on a substantially continuous basis attractive, light yellow colored blossoms. The vegetation is vigorous and the growth habit is very bushy and upright. Attractive glossy, dark green foliage is formed. The resistance to disease is very good. The new variety is particularly well suited for providing distinctive ornamentation in the landscape.

1 Drawing Sheet

Botanical/commercial classification:
Latin name—*Rosa hybrida.*
Common name—Grandiflora Rose Plant.
Varietal denomination—'KORmonali'.

SUMMARY OF THE INVENTION

The new variety of *Rosa hybrida* Grandiflora Rose Plant of the present invention was created by during May 2005 at Offenseth-Sparrieshoop, Germany by artificial pollination wherein two parents were crossed which previously had been studied in the hope that they would contribute the desired characteristics. The female parent (i.e., seed parent) of the new variety was the 'KORvanaber' variety (non-patented in the United States). The male parent (i.e., pollen parent) was the (unnamed seedling x 'KORassenet') variety (non-patented in the United States).

The parentage can be summarized as follows:

'KORvanaber' x (unnamed seedling x 'KORassenet')

The seeds resulting from the above pollination were sown and small plants were obtained which were physically and biologically different from each other. Selective study resulted in the identification of a single plant of the new variety.

It was found that the new Grandiflora Rose Plant of the present invention possesses the following combination of characteristics:

(a) abundantly and substantially continuously forms attractive, light yellow colored blossoms,
(b) exhibits a very bushy and upright growth habit,
(c) forms vigorous vegetation, (d) forms attractive ornamental glossy, dark green foliage, and
(e) exhibits very good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'KORvanaber' variety (i.e., seed parent) displays cream white colored flowers, whereas the new variety displays light yellow colored flowers that are larger in size with a higher petal count than that of the see parent. Additionally, the new variety displays (unnamed x 'KORassenet') variety (i.e., pollen parent) exhibits cream colored flower, whereas the new variety forms pink colored flowers with a higher petal count and has stronger vigor.

The new variety has been found to undergo asexual propagation in Klein Offenseth-Sparrieshoop, Germany by a number of routes such as budding. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORmonali'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately five years of age and was observed during July 2017 while budded on its own roots and growing outdoors at Ellerhoop, Germany.

FIG. 1—illustrates a specimen of a plant displaying blossoms.

DETAILED BOTANICAL DESCRIPTION

The chart used in the identification of colors is that of The Royal Horticultural Society (R.H.S. Colour Chart), 2015, London, England. The terminology which precedes reference to the chart has been added to indicate the corresponding color in more common terms. The description is based on the observation of three-year-old specimen of the new variety during July while growing in a three-gallon container on its own roots in Cochranville, Pa.

Class: Grandiflora Rose Plant.

Plant:

*Habit*.—Very bushy and rounded.

*Height*.—Commonly near 45.0 cm, measured from the top of the soil plane.

*Width*.—Commonly near 45.0 cm.

Branches:

*Color*.—Young stems: commonly near Yellow-Green Group 146C. Old wood: commonly near Grey-Brown Group 199D.

*Length*.—Main stem: approximately 30.0 cm on average. Secondary stems: approximately 10.0 cm on average.

*Thorns*.—Young thorns: color is commonly near Greyed-Orange Group 165A; length is approximately 1.0 cm on average; width is approximately 5.0 mm on average at point of attachment. Old thorns: color is commonly near Greyed-Green Group 197D; length is approximately 7.0 mm on average; width is approximately 5.0 mm on average at point of attachment.

Foliage:

*General appearance*.—Glossy, dark green.

*Young foliage color*.—Upper surface: commonly near Yellow-Green Group 144A with some highlights of Greyed-Purple Group 184A along the margins. Under surface: commonly near Greyed-Purple Group 184B.

*Old foliage color*.—Upper surface: commonly near Green Group 137A. Under surface: commonly near Green Group 137C.

*5-leaflet leaf*.—Length: approximately 10.0 cm on average. Width: approximately 10.5 cm on average.

Leaflets:

*Number*.—Commonly 3, 5, and 7.

*Shape*.—Ovate.

*Margin*.—Serrate.

*Texture*.—Upper surface and under surface: smooth.

*Terminal leaflet*.—Length: approximately 6.0 cm on average. Width: approximately 3.0 cm on average.

*Lower leaflet*.—Length: approximately 4.0 cm on average. Width: approximately 2.0 cm on average.

*Rachis*.—Color of upper surface: commonly near Green Group 137A. Color of under surface: commonly near Green Group 137C.

*Petiole*.—Texture of upper surface: smooth. Texture of under surface: glandular with some small prickles. Color of upper surface: commonly near Green Group 136A. Color of under surface: commonly near Green Group 137C.

*Stipules*.—Length: approximately 22.0 mm on average. Width: approximately 6.0 mm on average. Margin: entire to erose. Color of upper surface: commonly near Green Group 137C. Color of lower surface: commonly near Yellow-Green Group 146B.

Inflorescence:

*Number of flowers*.—Generally about 5 blooms on a plant at once, on average.

*Number of blossoms per stem*.—Commonly between 1 and 5 blooms per stem on average.

*Bud*.—Shape: ovoid. Length: approximately 1.5 cm on average. Width: approximately 1.5 cm on average. Color when opening: commonly near Green-Yellow Group 1C.

*Sepals*.—Number commonly 5. Length: approximately 2.5 cm on average. Width: approximately 1.0 cm on average. Margin: entire with occasional extensions on two or three sepals measuring 1.0 cm in length and 1.0 mm in width. Upper surface: Texture: covered in short pubescence. Color: commonly near Yellow-Green Group N144D. Under surface: Texture: puberulent. Color: commonly near Green Group 143C.

*Peduncle*.—Length: approximately 4.5 cm on average. Diameter: approximately 3.0 mm on average. Surface texture: sparely covered in short, flexible thorns that measure less than 2.0 mm in length. Color: commonly near Yellow-Green Group 144A.

*Flower*.—Form: double, cuplike. Diameter: approximately 7.0 cm on average. Color: upper surface and under surface commonly near Yellow Group 3D. Fragrance: very light sweet fragrance. Number of petals: approximately 20 on average. Petal drop: good. Shape of the petal: Overall: broadly obovate. Apex: round. Base: cuneate. Petal length: approximately 5.0 cm on average. Petal width: approximately 3.5 cm on average. Petal margin: entire. Petaloids number: commonly 5 per flower on average. Petaloids length: approximately 2.0 cm on average. Petaloids width: approximately 1.0 cm on average. Petaloids texture: smooth. Petaloid shape: variable, oblong and mostly curving inward. Apex: round. Base: cuneate. Petaloids margins: variable, entire to erose. Petaloid color: upper surface and under surface are commonly near Yellow Group 3D. Stamen: number is approximately 100. Anthers: number is approximately 100 on average and color is commonly near Yellow Group 13A. Filaments: length is approximately 1.0 cm on average and color is commonly near Yellow-Orange Group 14B. Pistils: arrangement is separate and free and number is approximately 54 on average. Style: length is approximately 9.0 mm on average and color is commonly near Red-Purple Group 63A. Stigma: diameter is less than 1.0 mm on average and color is commonly near Yellow-Orange Group 18A. Receptacle: achenes stand on the bottom and wall; diameter is approximately 1.0 cm on average; shape is round; surface texture is smooth; and color is commonly near Yellow-Green Group 144B. Pollen: not available at this stage. Hips: not available at this stage.

Development:

*Vegetation*.—Vigorous and glossy; dark green colored.

*Blooming*.—Abundant and substantially continuous from spring through frost.

*Tolerance to diseases*.—Very good. Plants of the 'KORmonali' variety have not been observed under all possible environmental conditions to date. Accordingly, it is possible that the phenotypic expression may vary somewhat with changes in light intensity and duration, cultural practices, and other environmental conditions.

I claim:

1. A new and distinct Grandiflora Rose Plant characterized by the following combination of characteristics:

(a) abundantly and substantially continuously forms attractive, light yellow colored blossoms, (b) exhibits a very bushy and upright growth habit, (c) forms vigorous vegetation, (d) forms attractive ornamental glossy, dark green foliage, and (e) exhibits very good disease resistance;

substantially as herein shown and described.

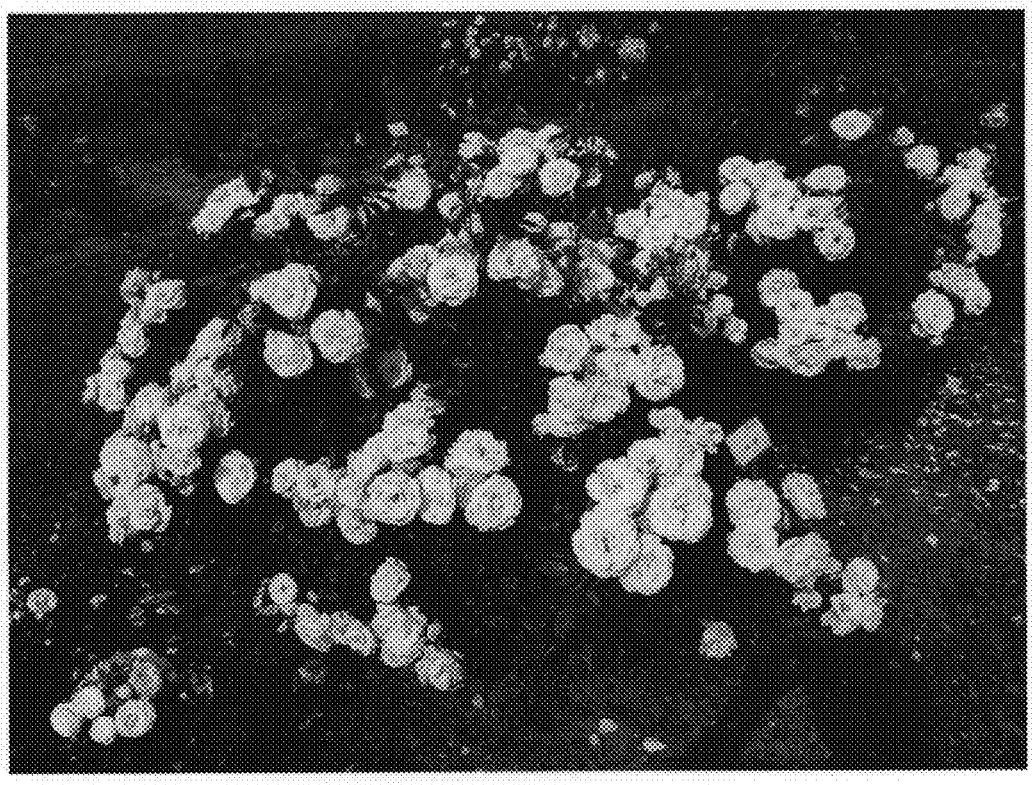

* * * * *